United States Patent [19]

Walsh et al.

[11] Patent Number: 4,503,073
[45] Date of Patent: Mar. 5, 1985

[54] 2-AMINO-3-(ALKYLTHIOBENZOYL)-PHENYLACETIC ACIDS

[75] Inventors: David A. Walsh; Dwight A. Shamblee, both of Richmond, Va.

[73] Assignee: A. H. Robins Company, Incorporated, Richmond, Va.

[21] Appl. No.: 554,420

[22] Filed: Nov. 22, 1983

Related U.S. Application Data

[63] Continuation-in-part of Ser. No. 222,870, Jan. 7, 1981, abandoned, which is a continuation of Ser. No. 68,029, Aug. 1, 1979, abandoned.

[51] Int. Cl.³ .................. C07C 149/43; A61K 31/24; A61K 31/195
[52] U.S. Cl. .......................... 514/539; 514/562; 560/9; 562/426
[58] Field of Search ............. 560/9, 36; 562/426; 424/309, 319

[56] References Cited

U.S. PATENT DOCUMENTS

| | | | |
|---|---|---|---|
| 3,828,093 | 8/1974 | Bays | 560/36 |
| 3,880,916 | 4/1975 | Dickel | 560/9 |
| 3,975,531 | 8/1976 | Welstead | 560/36 |
| 4,021,469 | 5/1977 | Weston | 560/9 |
| 4,045,575 | 8/1977 | Welstead | 424/309 |
| 4,126,635 | 11/1978 | Welstead | 424/309 |

FOREIGN PATENT DOCUMENTS 1521097  8/1978  United Kingdom ............... 424/309

OTHER PUBLICATIONS

Lowy, "An Introduction to Organic Chemistry," 4th Ed., pp. 198–199, (1936).

*Primary Examiner*—Michael L. Shippen

[57] ABSTRACT

Novel 2-amino-3-(alkylthiobenzoyl)phenylacetic acids, esters and metal salts have the formula:

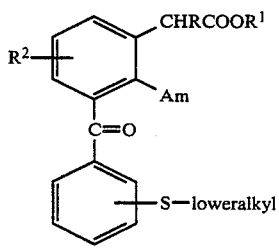

wherein R is hydrogen or lower alkyl, $R^1$ is hydrogen, lower alkyl or pharmaceutically acceptable metal cation, $R^2$ is hydrogen, halogen, lower alkyl or lower alkoxy, Am is primary amino ($-NH_2$), methylamino or dimethylamino. The compounds have anti-inflammatory activity; have effective analgesic activity, and inhibit blood platelet aggregation.

28 Claims, No Drawings

2-AMINO-3-(ALKYLTHIOBENZOYL)-PHENYLACETIC ACIDS

REFERENCE TO PARENT APPLICATIONS

This application is a continuation-in-part of U.S. patent application Ser. No. 222,870 filed Jan. 7, 1981, now abandoned, which is a continuation of U.S. patent application Ser. No. 068,029 filed Aug. 1, 1979, which application is now abandoned.

BACKGROUND OF THE INVENTION

1. Field of Invention

The present invention relates to certain novel 2-amino-3-benzoylphenylacetic acids having alkylthio substitution on the benzoyl moiety, their alkylesters and metal salts, pharmaceutical compositions and uses thereof and certain intermediates for the preparation thereof.

2. Information Disclosure Statement

Certain 2-amino-3-(5 and 6) benzoylphenylacetic acids having the benzoyl moiety substituted by lower alkyl, halogen, nitro and trifluoromethyl and methods of preparing and using the same are disclosed in U.S. Pat. No. 4,045,576. The compounds of the present invention cannot be prepared by the procedures disclosed therein.

2-Amino-3-benzoylphenylacetamides having a methylthio substituent on benzoyl are disclosed in U.S. Pat. No. 4,313,949.

SUMMARY OF THE INVENTION

The invention is more specifically concerned with 2-amino-3-(alkylthiobenzoyl)phenylacetic acids, alkylesters and metal salts having the formula:

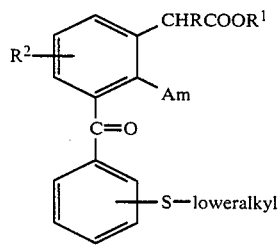

Formula I wherein;

R is hydrogen or lower alkyl, $R^1$ is hydrogen, lower alkyl or pharmaceutically acceptable metal cation, $R^2$ is hydrogen, halogen, lower alkyl or lower alkoxy, Am is primary amino(—$NH_2$), methylamio or dimethylamino.

The novel compounds of Formula I possess valuable pharmacological properties and are useful as pharmaceutical agents. The compounds exhibit anti-inflammatory and analgesic activity and inhibit blood platelet aggregation in warm-blooded animals.

Certain novel intermediates, the 7-(S-loweralkylthiobenzoyl)indolin-2-ones are represented by Formula II:

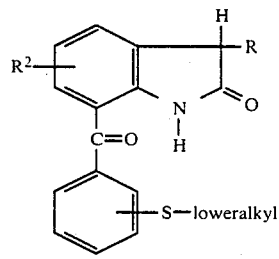

Formula II wherein R, $R^1$ and $R^2$ are as hereinabove defined.

The anti-inflammatory activity was demonstrated in laboratory animals using a modification of the Evans Blue Carrageenan Pleural Effusion Assay of Sancilio, L. F., J. Pharmacol. Exp. Ther. 168, 199–204 (1969).

The compounds of Formula I as inhibitors of blood platelet aggregation illustrate this property by the reduction of platelet aggregation as described by Born, J. of Phys. 162, 67–68 p. (1962) and Evans et al, J. of Expt. Med. 128, 877–894 (1968). Rats were orally administered test drugs and after 2 hrs. the rats were bled and platelet rich plasma obtained. Collagen was added to the platelet rich plasma to induce platelet aggregation and comparisons were made between control and treated samples.

The compounds of Formula I also act as analgetics as determined by the Bradykinin Analgetic Test method of Dickerson et al, Life Sci. 4, 2063–2069 (1965) as modified by Sancilio and Cheung, Fed. Proc. 35, 774 (1976).

It is therefore an object of the present invention to provide novel compounds and compositions. Another object is to provide methods for the preparation of the novel compounds. A still further object is to provide a novel method for the treatment of a living animal body and especially mammalian bodies for purposes of alleviating inflammation and pain and inhibiting blood platelet aggregation with a minimum of undesirable side effects. Additional objects will be apparent to one skilled in the art and still other objects will become apparent hereinafter.

DETAILED DESCRIPTION OF THE INVENTION

The present invention encompasses the compounds of Formula I set forth above with accompanying definitions as composition of matter and the utilization of these novel compounds in living animals for their pharmacological effects as set forth hereinabove and below.

In the definition of symbols in the formulas hereof and where they appear elsewhere throughout this specification, the terms have the following significance.

The term "lower alkyl" as used herein includes straight and branched chain radicals of up to six carbons inclusive, preferably no more than four carbon atoms, and is exemplified by such groups as methyl, ethyl, propyl, isopropyl, butyl, sec. butyl, tertiary butyl, amyl, isoamyl and hexyl. The term "lower alkoxy" has the formula —O-lower alkyl.

The term "halogen" when referred to herein is Cl, F, Br and I.

Illustrative of pharmaceutically acceptable salts are sodium, potassium, calcium, magnesium, zinc, copper and the hydrates thereof.

METHODS OF PREPARATION

The starting fluorobenzoylindolin-2-ones used to prepare the compounds of this invention may be prepared by one or more of the methods disclosed in U.S. Pat. No. 4,045,576. One method disclosed therein begins by reacting 2-amino-4'-halobenzoylbenzophenone with ethyl methylthioacetate, t-BuOCl and Et₃N to give 7-(halobenzoyl)-3-methylthioindolin-2-ones which are then reduced with Raney nickel to produce the 7-(halobenzoyl)-3-indolin-2-one. A modification of this procedure was used wherein Raney nickel was replaced by tin powder in alcohol and concentrated hydrochloric acid. The following equation is representative of the preparation of 7-(fluorobenzoyl)-indolin-2-ones used to prepare the compounds of the invention:

The preparation of the compounds of this invention is accomplished by reacting fluorobenzoyl indolin-2-ones with alkalimetal alkylsulfide, followed by acid hydrolysis to obtain the 7-(alkylthiobenzoyl)indolin-2-ones and hydrolyzing with alkali-metal base to give the alkali-metal salt of the 2-amino-3-(alkylthiobenzoyl)phenylacetic acids. The following reaction sequence illustrates the preparation of the alkali-metal salts of the compounds of Formula I:

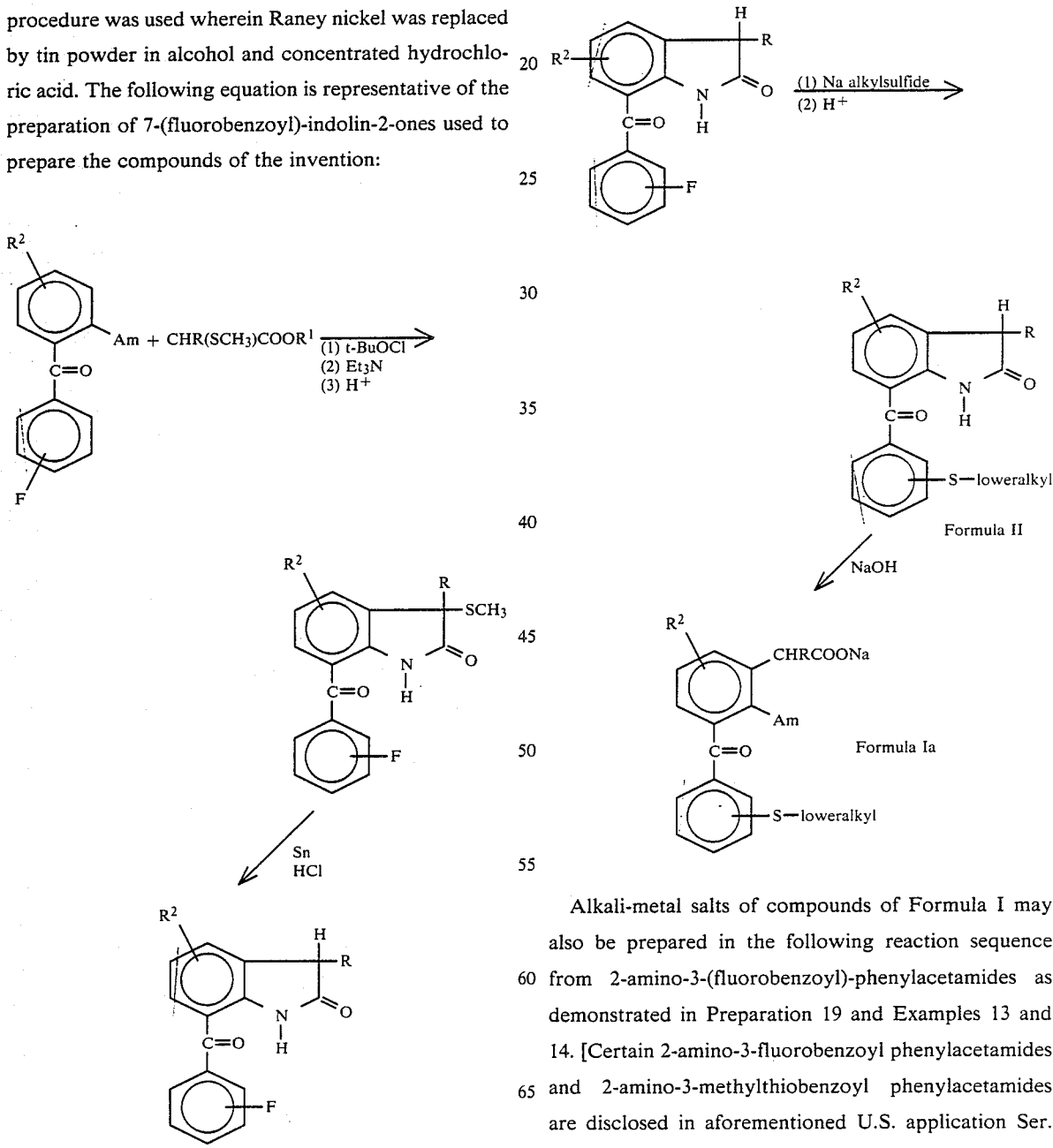

Alkali-metal salts of compounds of Formula I may also be prepared in the following reaction sequence from 2-amino-3-(fluorobenzoyl)-phenylacetamides as demonstrated in Preparation 19 and Examples 13 and 14. [Certain 2-amino-3-fluorobenzoyl phenylacetamides and 2-amino-3-methylthiobenzoyl phenylacetamides are disclosed in aforementioned U.S. application Ser. No. 507,259]:

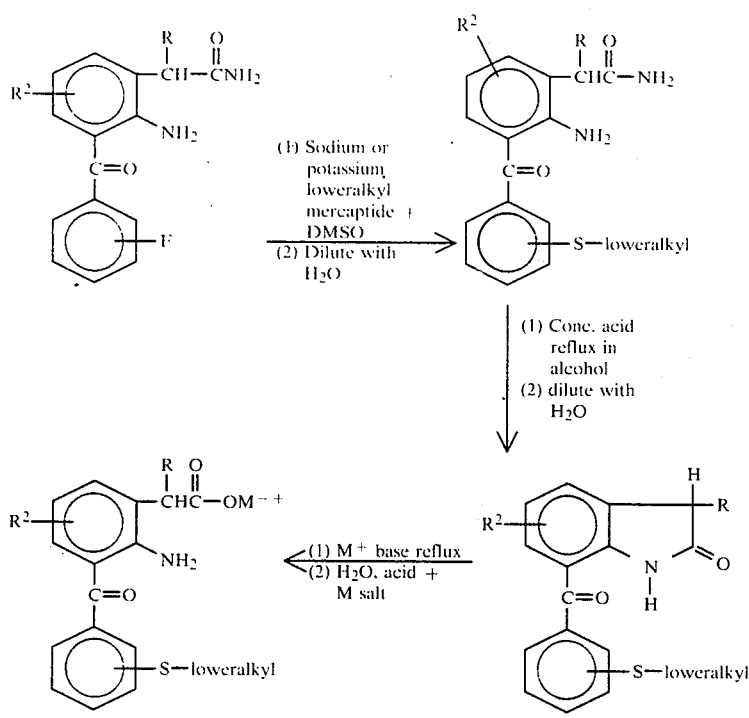

To obtain the free acid ($R^1$=H) from the alkali metal salt, acetic acid is carefully added to an aqueous solution of the salt which causes the free acid to precipitate. The free acid is then separated by filtration, washed with water and dried. To obtain the ester ($R^1$=loweralkyl), the alkali metal salt is treated in a suitable solvent such as dry dimethylformamide with lower alkyl iodide. Water is added and the ester extracted from the mixture with a suitable solvent such as diethyl ether, dried over sodium sulfate and solvent removed by evaporation.

The compounds of Formula I wherein Am is dimethylamino are prepared by reacting a 2-aminophenylacetic acid ester of Formula I wherein Am is —$NH_2$ with formaldehyde and sodium cyanoborohydride in a solvent such as acetonitrile under mildly acidic conditions as provided by the use of glacial acetic acid.

The reaction conditions employed for the preparation of the fluorobenzoylindolin-2-one starting materials is more specifically illustrated in the preparations which follow.

PREPARATION 1

7-(4-Fluorobenzoyl)-3-methylthioindolin-2-one

A solution of 42.2 g (0.196 mole) of 2-amino-4'-fluorobenzophenone in 2 liters of methylene chloride was cooled to −65° C. and 26.5 g (0.198 mole) of ethyl methylthioacetate was added. A solution of 23.0 g (0.21 mole) of 95% tertiary butoxychloride in 50 ml of methylene chloride was added dropwise, keeping the temperature below −65° C. One hour after the addition was complete, 22.2 g (0.22 mol) of triethylamine was added dropwise and the mixture was allowed to warm to room temperature. The solution was concentrated to 700 ml and then washed with water. The organic solution was concentrated and the residue dissolved in 400 ml of methanol containing 30 ml of concentrated hydrochloric acid. The mixture was heated at reflux for one hour followed by cooling. The mixture was allowed to stand overnight, the crystals collected and washed with methanol to yield 31.4 g (53%) as bright yellow solid, m.p. 165°-167.5° C.

Analysis: Calculated for $C_{16}H_{12}NO_2FS$: C,63.77; H,4.01; N,4.65; Found: C,63.58; H,4.11; N,4.67.

PREPARATION 2

Utilizing the procedure of Preparation B 1 but substituting for 2-amino-4'-fluorobenzophenone, equal molar amounts of the following:

2-amino-4'-fluoro-4-methylbenzophenone,
2-amino-4'-fluoro-5-methylbenzophenone,
2-amino-4'-fluoro-6-methylbenzophenone,
2-amino-4'-fluoro-4-chlorobenzophenone,
2-amino-4'-fluoro-6-chlorobenzophenone, there are obtained:

7-(4-fluorobenzoyl)-4-methyl-3-methylthioindolin-2-one,
7-(4-fluorobenzoyl)-5-methyl-3-methylthioindolin-2-one,
7-(4-fluorobenzoyl)-6-methyl-3-methylthioindolin-2-one,
7-(4-fluorobenzoyl)-4-chloro-3-methylthioindolin-2-one,
7-(4-fluorobenzoyl)-6-chloro-3-methylthioindolin-2-one.

PREPARATION 3

7-(4-Fluorobenzoyl)-5-methoxy-3-methylthioindolin-2-one

To a solution of 4.0 ml (0.088 mole) of chlorine in 200 ml of methylene chloride cooled to −70° C. is added dropwise a solution of 11.8 g (0.088 mole) of ethyl methylthioacetate in 30 ml of methylene chloride while maintaining the temperature below −65° C. After 5 min, a solution containing 0.2 mole of 2-amino-4'-fluoro-5-methoxybenzophenone in 100 ml of methylene chloride is added dropwise over a 30 min period. The mixture is stirred at −70° C. for about 1.5 hr and 18 g (0.18 mole) of triethylamine is added. The mixture is stirred for about an hour at −70° C. and then allowed to warm to ambient temperature. The mixture is treated with 30 ml of concentrated hydrochloric acid and stirred for about an hour. The mixture is filtered to remove some hydrochloric acid salt of starting 2-amino-4′-fluoro-5-methoxybenzophenone. The filtrate is washed with water and the organic layer is concentrated under reduced pressure. The residue is recrystallized from a suitable solvent; e.g., isopropyl alcohol and benzene, to give the title product.

PREPARATION 4

7-(2-Fluorobenzoyl)-3-methylthioindolin-2-one

A solution of 86 g (0.4 mole) of 2-amino-2′-fluorobenzophenone in 3 liters of methylene chloride was cooled to −65° C. and 54 g (0.4 mole) of ethyl methylthioacetate was added. A solution of 46 g (0.42 mole) of 95% tertiary butoxy chloride in 100 ml of methylene chloride was added dropwise, keeping the temperature below −65° C. One hour after addition was complete, 41 g (0.4 mole) of triethylamine was added dropwise and the mixture allowed to warm to room temperature. The solution was concentrated to about 1400 ml and then washed with water. The organic solution was concentrated and the residue dissolved in 800 ml methanol containing 60 ml of concentrated hydrochloric acid. The mixture was heated at reflux for one hour followed by cooling. The mixture stood overnight, then the crystals were collected and recrystallized from 20% aqueous ethanol to give 66 g (55%)pale yellow needles; m.p. 147.0°–148.5° C.

Analysis: Calculated for $C_{16}H_{12}NO_2FS$: C,63.77; H,4.01; N,4.65; Found: C,63.97; H,4.19; N,4.66.

PREPARATION 5

Utilizing the procedure of Preparation 4 but substituting for 2-amino-2′-fluorobenzophenone equal molar amounts of
2-amino-3′-fluorobenzophenone,
there is obtained:
7-(3-fluorobenzoyl)-3-methylthioindolin-2-one.

PREPARATION 6

7-(4-Fluorobenzoyl)indolin-2-one

A mixture of 40.0 g (0.133 mole) of 7-(4-fluorobenzoyl)-3-methylthioindolin-2-one and 40.0 g (0.34 mole) of tin powder in one liter of 95% ethanol was heated to reflux and 100 ml of concentrated hydrochloric acid was added. The mixture was heated for 6 hrs, then filtered while hot. The filtrate was cooled and the precipitate was collected and recrystallized from isopropyl alcohol to yield 24.5 g (72%) as off-white needles, m.p. 185°–187.0° C.

Analysis: Calculated for $C_{15}H_{10}NO_2F$: C,70.58; H,3.95; N,5.49; Found: C,70.80; H,4.12; N,5.51.

PREPARATION 7

Utilizing the procedure of Preparation 6 but substituting for 7-(4-fluorobenzoyl)-3-methylthioindolin-2-one, equal molar amounts of the following:
7-(4-fluorobenzoyl)-4-methyl-3-methylthioindolin-2-one,
7-(4-fluorobenzoyl)-5-methyl-3-methylthioindolin-2-one,
7-(4-fluorobenzoyl)-6-methyl-3-methylthioindolin-2-one,
7-(4-fluorobenzoyl)-4-chloro-3-methylthioindolin-2-one,
7-(4-fluorobenzoyl)-5-chloro-3-methylthioindolin-2-one,
7-(4-fluorobenzoyl)-6-chloro-3-methylthioindolin-2-one,
7-(4-fluorobenzoyl)-5-methoxy-3-methylthioindolin-2-one,
there are obtained:
7-(4-fluorobenzoyl)-4-methylindolin-2-one,
7-(4-fluorobenzoyl)-5-methylindolin-2-one,
7-(4-fluorobenzoyl)-6-methylindolin-2-one,
7-(4-fluorobenzoyl)-4-chloroindolin-2-one,
7-(4-fluorobenzoyl)-5-chloroindolin-2-one,
7-(4-fluorobenzoyl)-6-chloroindolin-2-one,
7-(4-fluorobenzoyl)-5-methoxyindolin-2-one.

PREPARATION 8

7-(2-Fluorobenzoyl)-indolin-2-one

A mixture of 60 g (0.2 mole) of 7-(2-fluorobenzoyl)-3-methylthioindolin-2-one and 60 g (0.5 mole) of tin powder in one liter of 95% ethanol was heated to reflux and 150 ml of concentrated hydrochloric acid was added. Heating was continued for 18 hrs, then the mixture was cooled and the precipitate was collected by decanting the slurry from the remaining tin and filtering the slurry. The filter cake was recrystallized twice from absolute ethanol to give 31 g (60%) white needles, m.p. 209°–210° C.

Analysis: Calculated for $C_{15}H_{10}NO_2F$: C,70.58; H,3.95; N,5.49; Found: C,70.31; H,4.08; N,5.56.

PREPARATION 9

Utilizing the procedure of Preparation 8 but substituting for 7-(2-fluorobenzoyl)-3-methylthioindolin-2-one equal molar amounts of the following:
7-(3-fluorobenzoyl)-3-methylthioindolin-2-one, there is obtained:
7-(3-fluorobenzoyl)indolin-2-one.

PREPARATION 10

Utilizing the procedure of Preparation 1 but substituting equal molar amounts of ethyl α-(methylthio) propionate for ethyl methylthioacetate, there is obtained:
7-(4-fluorobenzoyl)-3-methyl-3-methylthioindolin-2-one.

PREPARATION 11

Utilizing the procedure of Preparation 6 but substituting equal molar amount of 7-(4-fluorobenzoyl)-3-methyl-3-methylthioindolin-2-one, there is obtained:
7-(4-fluorobenzoyl)-3-methylindolin-2-one.

PREPARATION 12

5-Chloro-7-(4-fluorobenzoyl)-3-methylthioindolin-2-one

A solution of 54.0 g (0.216 mole) of 4-chloro-4′-fluoro-2-aminobenzophenone in 700 ml of methylene chloride was cooled to −65° C. and 30.5 g (0.227 mol) of ethyl-2-methylthioacetate was added. Twenty six (26) g (0.227 mol) of 95% tertiary butoxy chloride was added dropwise under stirring over a 20 minute period while maintaining the temperature of the solution at −65° C. The resulting light brown yellow solution was stirred at −70° C. for one hour and 25 g (0.25 mol) of triethylamine was added to the solution. This mixture was allowed to warm to room temperature and 400 ml of 3N HCl was added to the mixture. The resulting mixture was heated at reflux temperature under vigorous stirring for 2 hrs. The resulting organic phase was separated, washed with 100 ml of water and dried. The methylene chloride was evaporated and the residue triturated with diethyloxide. The resulting solid was collected by filtration, washed and dried to give 35.1 g of product. The product was crystallized to give 31.1 g (43%) of the titled compound as off-white crystals, mp. 202°–204° C.

Analysis: Calculated for $C_{16}H_{11}ClFNO_2S$: C,57.23; H,3.30; N,4.17; Found: C,57.35; H,3.30; N,4.26.

PREPARATION 13

5-Chloro-7-(4-fluorobenzoyl)indolin-2-one

A slurry of 30.5 g (0.091 mol) of 5-chloro-7-(4-fluorobenzoyl)-3-methylthioindolin-2-one in 2.5 l of tetrahydrofuran was stirred vigorously and treated with 285 g of wet Raney nickel for 6 minutes. The mixture was filtered and the filter cake obtained was washed with 200 ml of tetrahydrofuran. The resulting filtrate was evaporated to leave 20.2 g of residue. This residue was recrystallized from acetone to give 16.8 g (64%) of the titled compound as white, fluffy needles, mp. 222°–225° C.

Analysis: Calculated for $C_{15}H_9ClFNO_2$: C,62.19; H,3.13; N,4.84; Found: C,62.18, H,3.10; N,4.90.

PREPARATION 14

5-Fluoro-7-(4-fluorobenzoyl)-3-methylthioindolin-2-one

A solution of 46.6 g (0.2 mole) of 2-amino-4',5-difluorobenzophenone in 1300 ml of methylene chloride was cooled to −65° C. and 26.8 g (0.2 mole) of ethyl methylthioacetate was added. The cold mixture was stirred vigorously while 23.0 g (0.2 mole) of 95% tertiary butoxy chloride was added dropwise. The mixture was stirred at −70° C. for one hour, then 23 g (0.22 mole) of triethylamine was added. The mixture was allowed to warm to room temperature and 10 ml of concentrated hydrochloric acid was added. The mixture was heated at reflux with vigorous stirring for 2 hrs. The organic phase was separated and the residue was crystallized from ethyl acetate to give 28.9 g (45%) of the titled compound as off-white crystals, m.p. 171.0°–172.5° C.

Analysis: Calculated for $C_{16}H_{11}F_2NO_2S$: C,60.18; H,3.47; N,4.39 Found: C,60.10; H,3.46; N,4.47.

PREPARATION 15

5-Fluoro-7-(4-fluorobenzoyl)indolin-2-one

A slurry of 27.1 g (0.85 mole) of 5-fluoro-7-(4-fluorobenzoyl)-3-methylthioindolin-2-one in 500 ml of tetrahydrofuran was treated with 220 g of wet Raney nickel. The mixture was filtered and the filtrate was concentrated. The residue obtained was crystallized from acetone to give 14.8 g (64%) of the titled compound as light yellow crystals, m.p. 195°–196.5° C.

Analysis: Calculated for $C_{15}H_9F_2NO_2$: C,65.94; H,3.32; N,5.13; Found: C,65.93; H,3.28; N,5.18.

PREPARATION 16

N-[2-(4-Fluorobenzoyl)-4-methylphenyl]acetamide

A Grignard reagent prepared from 87.5 g (0.5 mole) of p-bromofluorobenzene and excess magnesium in 800 ml of diethyl ether was slowly added to a solution of 2,6-dimethyl-3,1-benzoxazine-4-one in 300 ml of dry benzene and 200 ml of dry diethyl ether at 0° C. The mixture was allowed to warm to room temperature and stirring was continued for 2 hr. The reaction mixture was cooled to −15° C. and 500 ml of 3N hydrochloric acid was added. After about 10 min additional stirring, the organic layer was separated and washed with dilute sodium hydroxide solution. The organic layer was concentrated and the residue was dissolved in a mixture of 600 ml of 95% ethanol and 300 ml of 6N hydrochloric acid. The precipitate (crude titled product) in the amount of 123 g (ca 91%) was recrystallized from cyclohexane to give tan crystals, m.p. 140°–145° C.

Analysis: Calculated for $C_{16}H_{14}FNO_2$: C,70.84; H,5.20; N,5.16; Found: C,71.17; H,5.33; N,5.00.

PREPARATION 17

(2-Amino-5-methylphenyl)(4-fluorophenyl)methanone

A solution of 119 g (0.44 mole of N-[2-(4-fluorobenzoyl)-4-methylphenyl]acetamide in 500 ml of 95% ethanol and 300 ml of 6N hydrochloric acid was heated at reflux for 16 hr. The solvents were removed on a rotoevaporator and the residue obtained was partitioned between concentrated ammonium hydroxide and benzene. The organic layer was concentrated and the new residue was chromatographed on silica gel, eluting with 10% ethyl acetate in hexane. The product fractions were concentrated and the residue was crystallized from a mixture of cyclohexane and hexane to give 56.3 g (61.5%) of the titled compound as bright yellow crystals, m.p. 70.0°–71.5° C.

Analysis: Calculated for $C_{14}H_{12}FNO$: C,73.35; H,5.28; N,6.11; Found: C,73.43; H,5.24; N,6.14.

PREPARATION 18

2-Amino-3-(4-fluorobenzoyl)-5-methyl-α-(propylthio)phenylacetamide

To a mixture of 45.8 g (0.2 mole) of (2-amino-5-methylphenyl)(4-fluorophenyl)methanone and 26.6 g (0.2 mole) of 2-(1-propylthio)acetamide and 700 ml of methylene chloride cooled to −70° C. was added 23 g (0.2 mole) of 95% t-butoxychloride over a 40 minute period. The mixture was kept at −70° C. for 2 additional hours and then 21 g (0.2 mole of triethylamine was added dropwise. The mixture was allowed to warm to room temperature and was washed with water. The organic layer was concentrated and the residue was triturated with isopropyl ether to give 61.7 g (86%) of the titled compound as yellow crystals, m.p. 130.5°–132.5° C.

Analysis: Calculated for $C_{19}H_{21}FN_2O_2S$: C,63.31; H,5.87; N,7.77 Found: C,63.09; H,5.76; N,7.73

PREPARATION 19

2-Amino-3-(4-fluorobenzoyl)-5-methylphenylacetamide

A mixture of 60.0 (0.167 mole) of 2-amino-3-(4-fluorobenzoyl)-5-methyl-α-(propylthio)phenylacetamide in 2.4 liters of tetrahydrofuran was treated with 400 g of wet Raney nickel (washed with water and titrated to constant pH 7 with acetic acid, washed again with water and then washed 3 times with tetrahydrofuran). The mixture was filtered and the filtrate was concentrated. The residue was triturated with hot isopropyl ether and recrystallized from isopropyl alcohol to give 43.6 (91%) of the titled compound as bright yellow crystals, m.p. 203°–206° C.

Analysis: Calculated for $C_{16}H_{15}FN_2O_2$: C,67.12; H,5.28; N,9.78; Found: C,67.14; H,5.32; N,9.76.

PREPARATION 20

2-Amino-5-methyl-3-[4-(methylthio)benzoyl]-phenylacetamide

A solution of 9.0 g (0.105 mole) of potassium methyl mercaptide in 75 ml of dimethylsulfoxide was added to a solution of 24.3 g (0.085 mole) of 2-amino-3-(4-fluorobenzoyl-5-methylphenylacetamide in 200 ml of dimethylsulfoxide. The mixture was stirred for 45 minutes, then poured into 2 liters of water. The solid which formed was collected by filtration and recrystallized from absolute ethanol to give 24.5 g (92%) of the titled compound as bright yellow needles, m.p. 187.5°–189.5° C.

Analysis: Calculated for $C_{17}H_{18}N_2O_2S$: C,64.94; H,5.77; N,8.91; Found: C,64.92; H,5.76; N,8.94.

The reaction conditions employed for preparing novel intermediates and compounds of the invention are more fully illustrated in the examples which follow.

EXAMPLE 1

7-(4-Methylthiobenzoyl)indolin-2-one

A solution of sodium methyl mercaptide, prepared from 400 ml of 3N sodium hydroxide and 24 g (0.5 mole) of methyl sulfide, was mixed with 25.5 g (0.1 mole) of 7-(4-fluorobenzoyl)indolin-2-one. The mixture was refluxed for 1.5 hr cooled and acidified (caution: much methyl sulfide evolves rapidly). The resulting precipitate was collected and recrystallized twice from benzene to give 17.8 g (70%) as yellow crystals, m.p. 167.0°–169.0° C.

Analysis: Calculated for $C_{16}H_{13}NO_2S$: C,67.82; H,4.63; N,4.94; Found: C,67.65; H,4.63; N,4.91.

EXAMPLE 2

Utilizing the procedure of Example 1 but substituting for 7-(4-fluorobenzoyl)indolin-2-one, equal molar amounts of the following:
7-(4-fluorobenzoyl)-4-methylindolin-2-one,
7-(4-fluorobenzoyl)-6-methylindolin-2-one,
7-(4-fluorobenzoyl)-4-chloroindolin-2-one,
7-(4-fluorobenzoyl)-6-chloroindolin-2-one,
7-(4-fluorobenzoyl)-5-methoxyindolin-2-one,
7-(2-fluorobenzoyl)-indolin-2-one,
7-(3-fluorobenzoyl)indolin-2-one,
there are obtained:
7-(4-methylthiobenzoyl)-4-methylindolin-2-one,
7-(4-methylthiobenzoyl)-6-methylindolin-2-one,
7-(4-methylthiobenzoyl)-4-chloroindolin-2-one,
7-(4-methylthiobenzoyl)-6-chloroindolin-2-one,
7-(4-methylthiobenzoyl)-5-methoxyindolin-2-one,
7-(2-methylthiobenzoyl)indolin-2-one, and
7-(3-methylthiobenzoyl)indolin-2-one.

EXAMPLE 3

Utilizing the procedure of Example 1 but substituting for sodium methyl mercaptide, equal molar amounts of the following:
sodium ethylmercaptide,
sodium isopropylmercaptide,
sodium-n-butylmercaptide,
there are obtained the following:
7-(4-ethylthiobenzoyl)indolin-2-one,
7-(4-isopropylthiobenzoyl)indolin-2-one,
7-(4-n-butylthiobenzoyl)indolin-2-one.

EXAMPLE 4

Sodium 2-amino-3-(4-methylthiobenzoyl)phenylacetic Acid Monohydrate

A mixture of 5.2 g (0.018 mole) of 7-(4-methylthiobenzoyl)indolin-2-one in 75 ml of 3N sodium hydroxide was heated at reflux for 20 hr. The red solution was cooled and a yellow precipitate formed. The precipitate was collected by filtration and washed with a small amount of cold water and then triturated with tetrahydrofuran. The precipitate was again separated by filtration, dried, and recrystallized from 95% ethanol to give 4.9 g (83%) bright yellow needles, m.p. 244°–247° C.

Analysis: Calculated for $C_{16}H_{14}NNaO_4S \cdot H_2O$: C,56.30; H,4.72; N,4.10; Found C,56.38; H,4.62; N,4.17.

EXAMPLE 5

Utilizing the procedure of Example 4 but substituting for 7-(4-methylthiobenzoyl)indolin-2-one, equal molar amounts of the following:
7-(4-methylthiobenzoyl)-4-methylindolin-2-one,
7-(4-methylthiobenzoyl)-6-methylindolin-2-one,
7-(4-methylthiobenzoyl)-4-chloroindolin-2-one,
7-(4-methylthiobenzoyl)-6-chloroindolin-2-one,
7-(4-methylthiobenzoyl)-5-methoxyindolin-2-one,
7-(2-methylthiobenzoyl)indolin-2-one,
7-(3-methylthiobenzoyl)indolin-2-one,
7-(4-ethylthiobenzoyl)indolin-2-one,
7-(4-isopropylthiobenzoyl)indolin-2-one, and
7-(4-n-butylthiobenzoyl)indolin-2-one,
there are obtained:
Sodium 2-amino-3-(4-methylthiobenzoyl)-6-methyl-phenylacetic acid,
Sodium 2-amino-3-(4-methylthiobenzoyl)-4-methyl-phenylacetic acid,
Sodium 2-amino-3-(4-methylthiobenzoyl)-6-chloro-phenylacetic acid,
Sodium 2-amino-3-(4-methylthiobenzoyl)-4-chloro-phenylacetic acid,
Sodium 2-amino-3-(4-methylthiobenzoyl)-5-methoxy-phenylacetic acid,
Sodium 2-amino-3-(2-methylthiobenzoyl)-phenylacetic acid,
Sodium 2-amino-3-(3-methylthiobenzoyl)-phenylacetic acid,
Sodium 2-amino-3-(4-ethylthiobenzoyl)-phenylacetic acid,
Sodium 2-amino-3-(4-isopropylthiobenzoyl)-phenylacetic acid, and
Sodium-amino-3-(4-n-butylthiobenzoyl)-phenylacetic acid.

EXAMPLE 6

7-(4-Methylthiobenzoyl)-3-methylindolin-2-one

Utilizing the procedure of Example 1 but substituting 7-(4-fluorobenzoyl)-3-methyl)indolin-2-one for 7-(4-fluorobenzoyl)indolin-2-one, the titled compound is obtained.

EXAMPLE 7

Sodium 2-amino-3-(4-methylthiobenzoyl)-α-methylphenylacetic acid

A suspension of 7-(4-methylthiobenzoyl)-3-methylindolin-2-one in 3N sodium hydroxide is refluxed under nitrogen, stripped of water under vacuum, and the product is isolated by trituration with organic solvent.

EXAMPLE 8

Ethyl 2-amino-3-(4-methylthiobenzoyl)phenylacetate

Seventeen grams (0.05 mole) of sodium 2-amino-3-(4-methylthiobenzoyl)phenylacetic acid monohydrate are dissolved in approximately 150 ml of dimethylformamide and the solution treated with 33 g ethyl iodide. The solution is stirred at room temperature for 2.5 hrs. and added to water and the mixture extracted several times with benzene. The combined benzene extracts are washed with dilute base and water, dried over sodium sulfate and concentrated to obtain the titled compound.

EXAMPLE 9

5-Chloro-7-(4-methylthiobenzoyl)indolin-2-one

A quantity of 9.8 g (33.8 mmol) of 5-chloro-7-(4-fluorobenzoyl)indolin-2-one was added to a stirred solution of 3.6 g (42.2 mmol) of potassium methyl mercaptide in 60 ml of dimethylsulfoxide resulting in an intense red solution. This solution was stirred at room temperature for one hour, then poured into 800 ml of water. The precipitate obtained was collected by filtration. This solid was dissolved in 800 ml of an organic solvent, treated with charcoal twice and then filtered. The filtrate obtained was evaporated to give a solid which was recrystallized to give 7.3 g (68%) of the titled compound as light orange crystals, m.p. 179°–181° C. An additional 0.9 g of the titled compound was recovered from the mother liquor giving a total yield of 8.2 g (76%).

Analysis: Calculated for $C_{16}H_{12}ClNO_2S$: C,60.47; H,3.81; N,4.41 Found: C,60.63; H,3.82; N,4.69.

EXAMPLE 10

Sodium 2-amino-5-chloro-3-(4-methylthiobenzoyl)phenylacetate hydrate [4:3]

A mixture of 6.4 g (20.0 mmol) of 5-chloro-7-(4-methylthiobenzoyl)indolin-2-one in 110 ml of 3N sodium hydroxide was heated at 100° C. in an oil bath and stirred under a nitrogen atmosphere for 22 hrs. The reaction mixture was diluted to 600 ml with water and then titrated to a pH of 7.5 with concentrated hydrochloric acid. The mixture was then filtered and the filter cake was extracted with 1.5 liter of hot water. The filtrate obtained was concentrated to a solid residue. This residue was dissolved in hot absolute ethyl alcohol and filtered. The filtrate obtained was concentrated to a solid which was dissolved in 300 ml of 2-propanol and filtered. The filtrate obtained was concentrated to 200 ml and cooled to 0° C., whereby a gel was obtained. This gel was left at room temperature and a crystalline solid was collected therefrom by filtration and dried to give 2.9 g (39%) of the titled compound as a yellow solid, m.p. 259°–260° C.

Analysis: Calculated for $C_{16}H_{13}ClNNaO_3S \cdot 0.75 H_2O$; C,51.76; H,3.94; N,3.77; Found: C,51.63; H,3.98; N,3.79.

EXAMPLE 11

5-Fluoro-7-(4-methylthiobenzoyl)indolin-2-one

A solution of 2.73 g (0.01 mol) of 5-fluoro-7-(4-fluorobenzoyl)indolin-2-one in 50 ml of dimethylsulfoxide was treated dropwise with a solution of 0.9 g (0.0105 mol) of potassium methyl mercaptide in 8 ml of dimethylsulfoxide and the mixture was stirred for 16 hours. The mixture was then poured into a solution of 10 ml of ethyl alcohol in 150 ml of water and the resulting yellow precipitate was collected and dried. The 2.5 grams of solid obtained was chromatographed on 200 g of silica gel, eluting with 2% acetone in methylene chloride. The product fractions were concentrated and the residue was recrystallized from isopropyl alcohol to give 1.8 g (60%) of the titled compound as pink-tan needles, m.p. 168°–174° C.

Analysis: Calculated for $C_{16}H_{12}FNO_2S$: C,63.77; H,4.01; N,4.65; Found: C,63.75; H,3.99; N,4.71.

EXAMPLE 12

Sodium 2-amino-5-fluoro-3-[4-(methylthio)benzoyl]phenylacetate

A mixture of 10.2 g (0.034 mol) of 5-fluoro-7-(4-methylthiobenzoyl)indolin-2-one and 150 ml of 3N sodium hydroxide was heated under a nitrogen atmosphere at 100° C. for 23 hours. The mixture was diluted to one liter with water and titrated with concentrated hydrochloric acid to a pH of 7.5. The mixture was filtered and the solid obtained was rinsed with hot water until no further dissolution was occurring. The filtrates were combined and concentrated and the residue was dried. A yellow residue was obtained and then dissolved in isopropyl alcohol and the solution was filtered. The filtrate obtained was concentrated to give 8.7 g (75%) of the titled compound as a yellow powder, m.p. 241°–244° C.

Analysis: Calculated for $C_{16}H_{13}FNNaO_3S$: C,56.30; H,3.84; N,4.10; Found: C,55.54; H,3.91; N,4.00.

EXAMPLE 13

5-Methyl-7-[4-(methylthio)benzoyl]-indolin-2-one

A solution of 18.8 g (0.06 mole) of 2-amino-5-methyl-3-[4-(methylthio)benzoyl]phenylacetamide in 1700 ml of absolute ethanol with 16.6 ml (0.2 mol) of concentrated hydrochloric acid was heated at reflux for 45 min. The mixture was diluted with 50 ml of water and cooled. The precipitate was collected and recrystallized from 60% aqueous ethanol to give 11.0 g (62%) of the titled compound as tan crystals, m.p. 176.0°–177.5° C.

Analysis: Calculated for $C_{17}H_{15}NO_2S$: C,68.66; H,5.08; N,4.71; Found: C,68.42; H,5.07; N,4.82.

EXAMPLE 14

Sodium 2-amino-5-methyl-3-(4-methylthiobenzoyl)phenylacetate dihydrate

A mixture of 8.9 g (0.03 mole) of 5-methyl-7-[4-(methylthio)benzoyl]indolin-2-one in 120 ml of 3N sodium hydroxide was heated at reflux for 16 hr. The mixture was diluted to 600 ml volume with water and the solution was titrated to pH 8.2 with concentrated hydrochloric acid. Solid sodium chloride was added to cause precipitation. The solid was collected by filtration and dissolved in hot absolute ethanol. The mixture was filtered and the filtrate was concentrated. The residue was dissolved in 500 ml of water. The solution was cooled to 0° C. and the precipitate was collected and dried to yield 3.8 g (37%) of the titled compound as orange-yellow powder, m.p. 255°–260° C. (decomposition).

Analysis: Calculated for $C_{17}H_{16}NO_3SNa.2H_2O$: C,54.68; H,5.40; N,3.75; Found: C,54.46; H,5.57; N,3.74.

FORMULATION AND ADMINISTRATION

The present invention also contemplates novel compositions containing the compounds of the invention as active ingredients. Effective quantities of any of the foregoing pharmacologically active compounds may be administered to a living animal body in any one of various ways, for example, orally as in capsules or tablets, parenterally in the form of sterile solutions or suspensions, and in some cases intravenously in the form of sterile solutions. In forming the novel compositions of this invention, the active ingredient is incorporated in a suitable carrier, illustratively, a pharmaceutical carrier. Suitable pharmaceutical carriers which are useful in formulating the compositions of this invention include starch, gelatin, glucose, magnesium carbonate, lactose, malt and the like. Liquid compositions are also within the purview of this invention and suitable liquid pharmaceutical carriers include ethyl alcohol, propylene glycol, glycerine, glucose syrup and the like.

The pharmacologically active compounds may be advantageously employed in a unit dosage of from 0.1 to 150 milligrams. The unit dosage may be administered once daily or in multiple or divided daily doses. The daily dosage may vary from 0.3 to 450 milligrams. Five to 25 milligrams appears optimum per unit dose.

It is only necessary that the active ingredient constitute an effective amount, i.e., such that a suitable effective dosage will be obtained consistent with the dosage form employed. The exact individual dosages as well as daily dosages will, of course, be determined according to standard medical principles under the direction of a physician or veterinarian.

The active agents of the invention may be combined with other pharmacologically active agents, or with buffers, antacids or the like, for administration and the proportion of the active agent in the composition may be varied widely.

The following are examples of compositions formed in accordance with this invention.

1. Capsules

Capsules of 5 mg., 25 mg., and 50 mg. of active ingredient per capsule are prepared. With the higher amounts of active ingredient, adjustment may be made in the amount of lactose.

| Typical blend for encapsulation | Per capsule, mg. |
|---|---|
| Active ingredient | 5.0 |
| Lactose | 296.7 |
| Starch | 129.0 |
| Magnesium stearate | 4.3 |
| Total | 435.0 mg. |

Additional capsule formulations preferably contain a higher dosage of active ingredient and are as follows:

| Ingredients | Per capsule, mg. |
|---|---|
| Active ingredient | 25.0 |
| Lactose | 306.5 |
| Starch | 99.2 |
| Magnesium stearate | 4.3 |
| Total | 435.0 mg. |

In each case, uniformly blend the selected active ingredient with lactose, starch, and magnesium stearate and encapsulate the blend.

2. Tablets

A typical formulation for a tablet containing 5.0 mg. of active ingredient per tablet follows. The formulation may be used for other strengths of active ingredient by adjustment of weight of dicalcium phosphate.

|  | Per tablet, mg. |
|---|---|
| (1) Active ingredient | 5.0 |
| (2) Corn starch | 13.6 |
| (3) Corn starch (paste) | 3.4 |
| (4) Lactose | 79.2 |
| (5) Dicalcium phosphate | 68.0 |
| (6) Calcium stearate | 0.9 |
|  | 170.1 mg |

Uniformly blend 1, 2, 4 and 5. Prepare 3 as a 10 percent paste in water. Granulate the blend with starch paste and pass the wet mass through an eight mesh screen. The wet granulation is dried and sized through a twelve mesh screen. The dried granules are blended with the calcium stearate and pressed.

3. Injectable—2% sterile solutions

|  | Per cc |
|---|---|
| Active ingredient | 20 mg. |
| Preservative, e.g., cholorobutanol | 0.5% weight/volume |
| Water for injection | q.s. |

Prepare solution, clarify by filtration, fill into vials, seal and autoclave.

Various modifications and equivalents will be apparent to one skilled in the art and may be made in the compounds, compositions, and methods of the present invention without departing from the spirit or scope thereof and it is therefore to be understood that the invention is to be limited only by the scope of the appended claims.

What is claimed is:

1. A compound selected from the group having the formula:

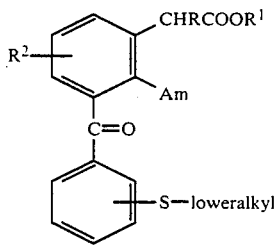

wherein;

R is selected from hydrogen or lower alkyl,

R[1] is selected from hydrogen, loweralkyl, or pharmaceutically acceptable metal cation, R[2] is hydrogen, halogen, loweralkyl or lower alkoxy, Am is primary amino (—NH$_2$), methylamino or dimethylamino.

2. The compound of claim 1 which is 2-amino-3-(4-methylthiobenzoyl)-phenylacetic acid or a pharmaceutically acceptable salt thereof.

3. The compound of claim 1 which is sodium 2-amino-3-(4-methylthiobenzoyl)-phenylacetate monohydrate.

4. The compound of claim 1 which is 2-amino-5-chloro-3-(4-methylthiobenzoyl)-phenylacetic acid or a pharmaceutically acceptable salt thereof.

5. The compound of claim 1 which is sodium 2-amino-5-chloro-3-(4-methylthiobenzoyl)-phenylacetate hydrate [4:3].

6. The compound of claim 1 which is 2-amino-5-fluoro-3-(4-methylthiobenzoyl)-phenyl acetic acid or a pharmaceutically acceptable salt thereof.

7. The compound of claim 1 which is sodium 2-amino-5-fluoro-3-(4-methylthiobenzoyl)phenylacetate.

8. The compound of claim 1 which is 2-amino-5-methyl-3-(4-methylthiobenzoyl)-phenylacetic acid or a pharmaceutically acceptable salt thereof.

9. The compound of claim 1 which is sodium 2-amino-5-methyl-3-(4-methylthiobenzoyl)-phenylacetate dihydrate.

10. A method of alleviating inflammation in a living animal body comprising internally administering to said living animal body an effective amount of a compound selected from the group having the formula:

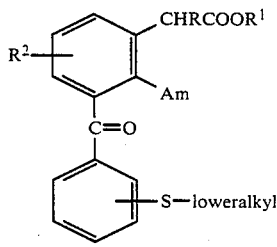

wherein;

R is selected from hydrogen or lower alkyl,

R[1] is selected from hydrogen, loweralkyl or pharmaceutically acceptable metal cation, R[2] is hydrogen, halogen, loweralkyl or lower alkoxy, Am is primary amino (—NH$_2$), methylamino or dimethylamino.

11. The method of claim 10 wherein the compound is 2-amino-3-(4-methylthiobenzoyl)-phenylacetic acid.

12. The method of claim 10 wherein the compound is sodium 2-amino-3-(4-methylthiobenzoyl)-phenylacetate monohydrate.

13. The method of claim 10 wherein the compound is 2-amino-5-chloro-3-(4-methylthiobenzoyl)phenylacetic acid or a pharmaceutically acceptable salt thereof.

14. The method of claim 10 wherein the compound is sodium 2-amino-5-chloro-3-(4-methylthiobenzoyl)-phenylacetate hydrate [4:3].

15. The method of claim 10 wherein the compound is 2-amino-5-fluoro-3-(4-methylthiobenzoyl)-phenylacetic acid or a pharmaceutically acceptable salt thereof.

16. The method of claim 10 wherein the compound is sodium 2-amino-5-fluoro-3-(4-methylthiobenzoyl)-phenylacetate.

17. The method of claim 10 wherein the compound is 2-amino-5-methyl-3-(4-methylthiobenzoyl)-phenylacetic acid or a pharmaceutically acceptable salt thereof.

18. The method of claim 10 wherein the compound is sodium 2-amino-5-methyl-3-(4-methylthiobenzoyl)phenylacetate dihydrate.

19. A therapeutic composition suitable for alleviating inflammation in a living animal body comprising (a) an effective amount of a compound selected from the group having the formula:

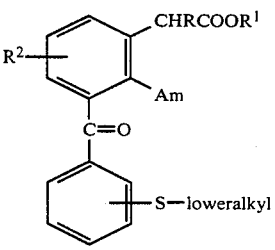

wherein;

R is selected from hydrogen or loweralkyl,

R[1] is selected from hydrogen, loweralkyl or pharmaceutically acceptable metal cation, R[2] is hydrogen, halogen, loweralkyl or lower alkoxy, Am is primary amino (—NH$_2$), methylamino or dimethylamino, and (b) a pharmaceutically acceptable carrier therefor.

20. The composition as defined in claim 19 wherein the compound is present in an amount of between about 0.1 and 150 milligrams.

21. The composition as defined in claim 19 wherein the compound is 2-amino-3-(4-methylthiobenzoyl)-phenylacetic acid.

22. The composition as defined in claim 19 wherein the compound is sodium 2-amino-3-(4-methylthiobenzoyl)-phenylacetate monohydrate.

23. The composition as defined in claim 19 wherein the compound is 2-amino-5-chloro-3-(4-methylthiobenzoyl)phenylacetic acid or a pharmaceutically acceptable salt thereof.

24. The composition as defined in claim 19 wherein the compound is sodium 2-amino-5-chloro-3-(4-methylthiobenzoyl)phenylacetate hydrate [4:3].

25. The composition as defined in claim 19 wherein the compound is 2-amino-5-fluoro-3-(4-methylthiobenzoyl)phenylacetic acid or a pharmaceutically acceptable salt thereof.

26. The composition as defined in claim 19 wherein the compound is sodium 2-amino-5-fluoro-3-(4-methylthiobenzoyl)phenylacetate.

27. The composition as defined in claim 19 wherein the compound is 2-amino-5-methyl-3-(4-methylthiobenzoyl)phenylacetic acid or a pharmaceutically acceptable salt thereof.

28. The composition as defined in claim 19 wherein the compound is sodium 2-amino-5-methyl-3-(4-methylthiobenzoyl)phenylacetate dihydrate.

* * * * *